United States Patent [19]

Dual et al.

[11] Patent Number: 4,920,787

[45] Date of Patent: May 1, 1990

[54] VISCOMETER

[76] Inventors: Jurg Dual, Bergstrasse 5, Zurich, Switzerland, CH-8044; Mahir Sayir, Im Straler 7, Zurich, Switzerland, CH-8047; Joseph Goodbread, Grossmannstrasse 34, Zurich, Switzerland, CH-8049

[21] Appl. No.: 197,990

[22] Filed: May 24, 1988

[30] Foreign Application Priority Data

Jun. 12, 1987 [CH] Switzerland .......................... 2220/87
Feb. 26, 1988 [CH] Switzerland ............................ 730/88

[51] Int. Cl.$^5$ ............................................ G01N 11/16
[52] U.S. Cl. ........................................................ 73/54
[58] Field of Search ........................ 73/54, 59, 60, 579; 310/369

[56] References Cited

U.S. PATENT DOCUMENTS

| | | | |
|---|---|---|---|
| 2,267,317 | 12/1941 | Veenschoten | 73/59 |
| 2,679,157 | 3/1954 | Carpenter | 73/59 |
| 2,819,610 | 1/1958 | White | 73/59 |
| 3,177,705 | 4/1965 | Bank | 73/54 |
| 3,611,789 | 10/1971 | Lopas | 73/59 |
| 3,710,614 | 1/1973 | Oppliger | 73/54 |
| 3,872,411 | 3/1975 | Watanabe et al. | 310/369 |
| 3,986,388 | 10/1976 | Stalzy | 73/59 |
| 4,005,599 | 2/1977 | Schletter et al. | 73/59 |
| 4,117,716 | 10/1978 | Simon | 73/54 |
| 4,240,285 | 12/1980 | Langdon | 73/32 A |
| 4,524,610 | 6/1985 | Fitzgerald et al. | 73/54 |
| 4,552,012 | 11/1985 | Bohlin | 73/59 |
| 4,741,200 | 5/1988 | Hammerle | 310/369 |

FOREIGN PATENT DOCUMENTS 2435707 4/1980 France .
2001761 2/1979 United Kingdom .
2071324 9/1981 United Kingdom .

OTHER PUBLICATIONS

"Vibrating Wire Viscosimeter", Rev. Sci. Instrum., vol. 46, No. 11, Nov. 1975.
"Vibratory Process Control Transducers", The Marconi Review, Band 43, Nr. 218, 1980.
"Application of the Birnboim Multiple Lumped Resonator Principle to Viscoelastic Measurements of Dilute Macromolecular Solutions", The Review of Scientific Instruments, Band 42, Nr. 2, Feb. 1971.
W. H. Robinson, "Piezoelectric Method of Determining Viscosity at 40 KHz", Journal of Applied Physics, Band 49, Nr. 3, Mar. 1978.

Primary Examiner—Hezron E. Williams
Assistant Examiner—Joseph W. Roskos
Attorney, Agent, or Firm—Powell L. Sprunger

[57] ABSTRACT

A resonator in the form of a cylindrical body is immersed in a fluid to be measured and excited by a piezoelectric transducer in the vicinity of its natural frequency. The vibration frequency is stabilized by a feedback loop. In that feedback loop a phase shift is introduced which can be switched between to discrete values. The resulting difference in frequency of oscillation of the resonator is proportional to the damping ratio of the resonator and is, therefore, a measure for the viscosity of the fluid. The natural frequency of the piezoelectric transducer is substantially higher than the natural frequency of the resonator, and the oscillation of the resonator is mechanically isolated from the housing by an inertial mass - spring arrangement with low natural frequency.

10 Claims, 6 Drawing Sheets

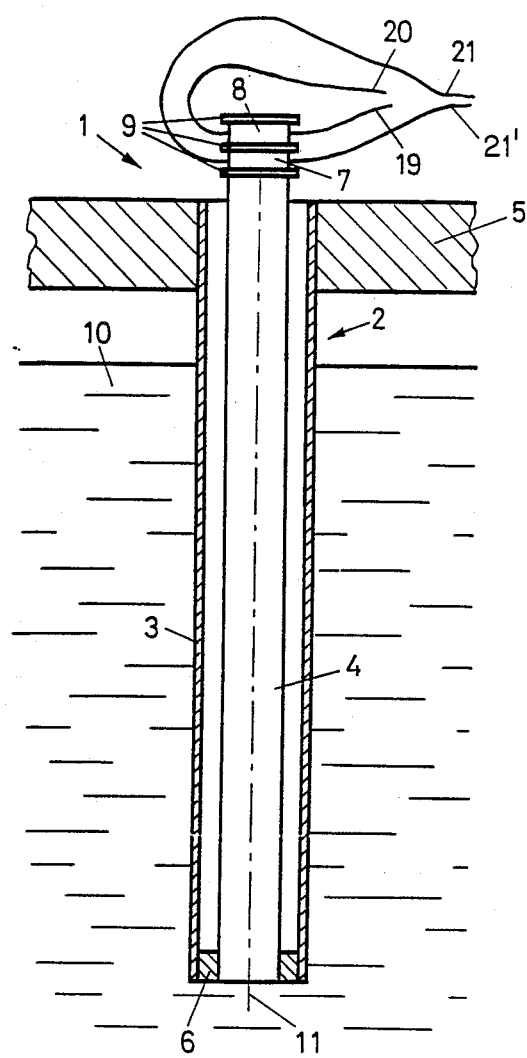
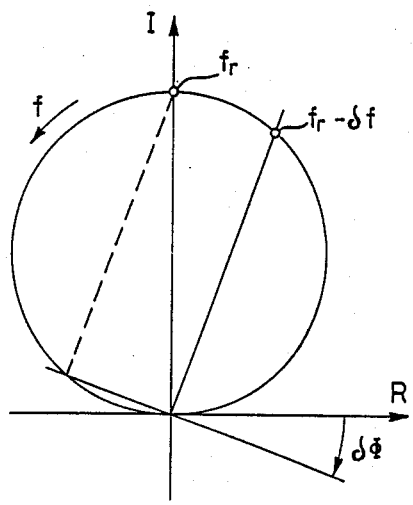
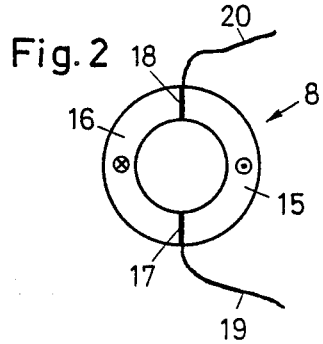
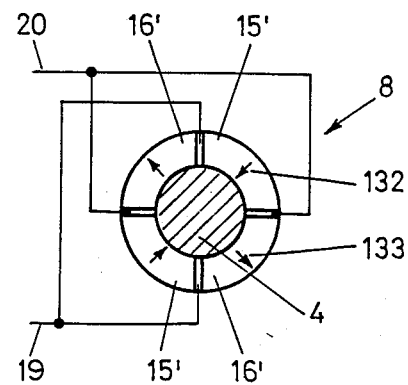

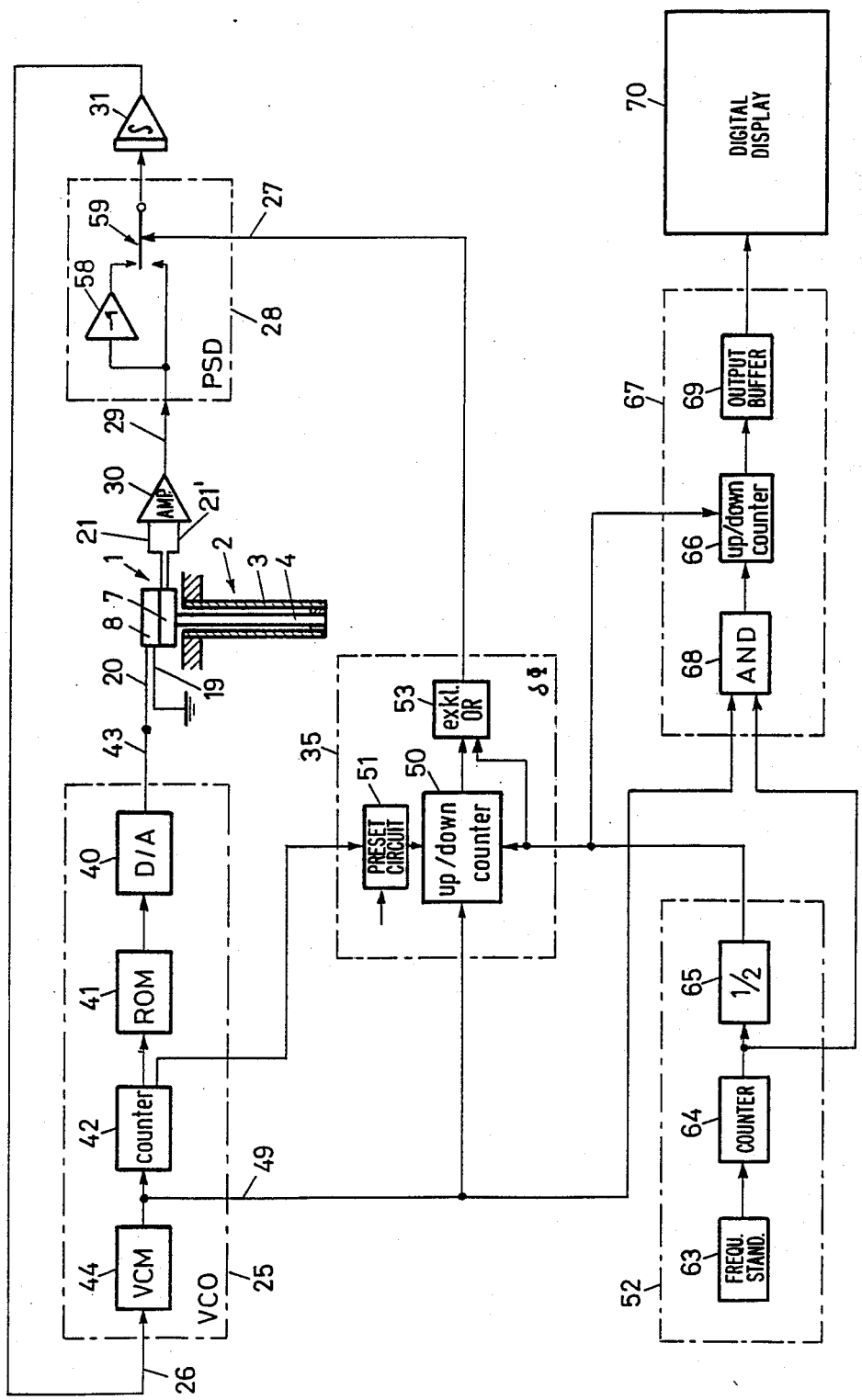

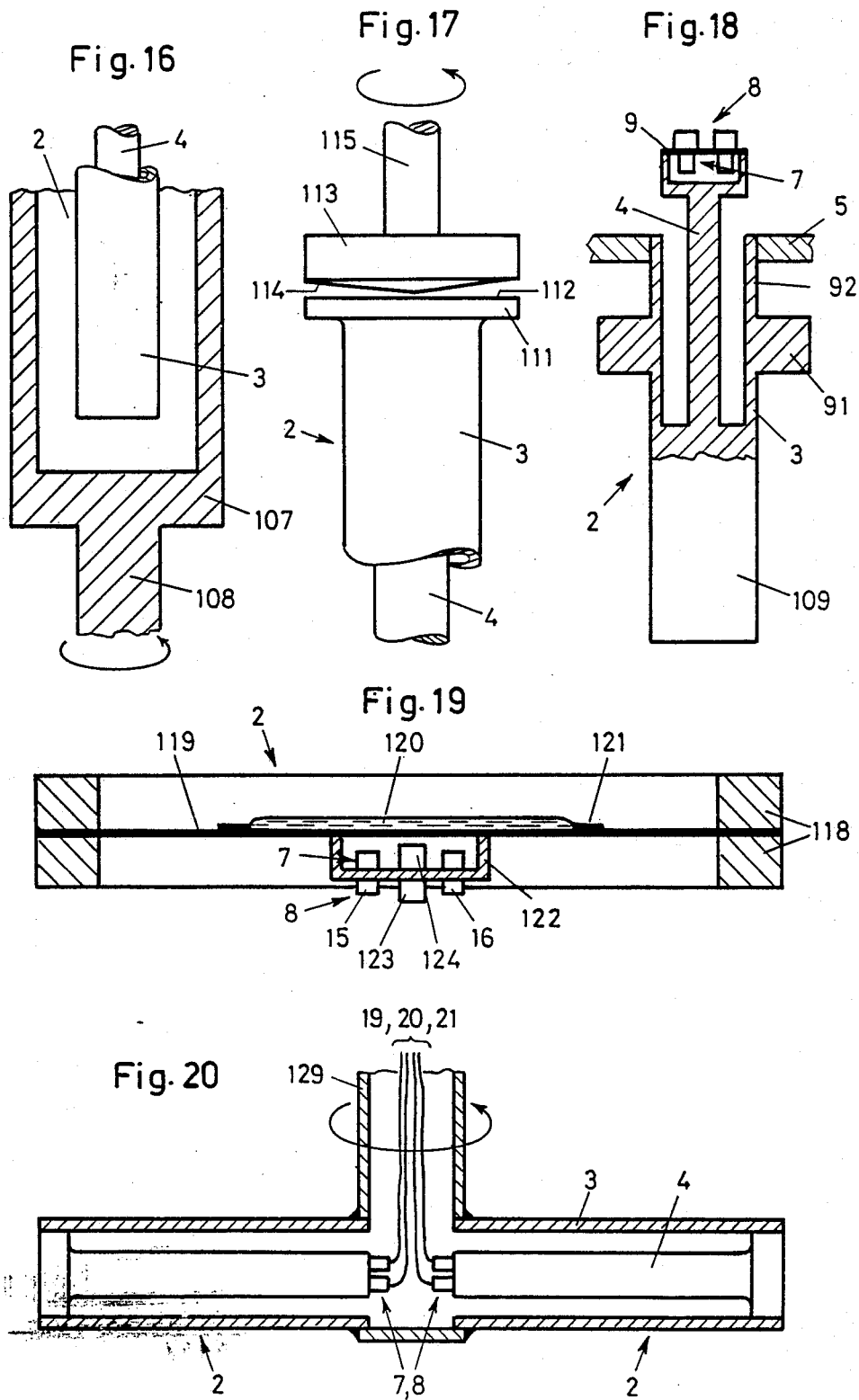

VISCOMETER

BACKGROUND OF THE INVENTION

The present invention relates to viscometers. The present application claims priority of Swiss applications 2220/87, filed June 12, 1987, and 730/88-0, filed February 26, 1988, incorporated herein by reference.

A viscometer is described in an article by John L. Schrag and Robert M. Johnson in "The Review of Scientific Instruments", Vol. 42 Nr.2, February 1971, Page 224. In the realization described in the article a resonator consisting of a rotationally symmetric body with several inertial masses and torsional springs arranged in series along its axis is excited by an oscillator in the neighborhood of one of its resonant frequencies. This frequency is varied in a certain range about the resonance, and for each frequency, the phase angle between the oscillator output and the torsional motion of the resonator is measured. The damping and therefore also the viscosity of the fluid can be determined from the resulting curve. In spite of the large investment in apparatus which this device requires, it offers only modest accuracy in a relatively narrow range of viscosities. Although it is suited for laboratory measurements, it is not useable for continuous measurements in industrial production processes.

A further measurement device for measurement of viscosity is described in an article by William H. Robinson in the "Journal of Applied Physics", Vol. 49, March 1978, page 1070 ff. A resonator in the form of a cylindrical quartz rod is excited at one of its torsional resonant frequencies by means of a piezoelectric transducer. A second transducer measures the changes in vibrational amplitude and frequency due to the fluid. The resonator rod is immersed to half its length in the fluid. It is sealed into the wall of the vessel containing the fluid by means of an O-ring seal at one of its vibrational nodal points. This device, too, is mainly useful for measurements under laboratory conditions. The evaluation of the measurement is demanding, and requires calibration measurements with fluids with known viscosities.

Further viscometers are known from U.S. Pat. Nos. 4,005,599 and 3,986,388. A rotationally symmetric rotor with domed ends is suspended coaxially in a cylindrical housing by means of four flexural springs. A rod-shaped magnet is mounted in the rotor perpendicular to its axis of rotation. The rotor can be caused to vibrate at a frequency near to its resonant frequency by means of electromagnetic coils mounted in the housing. A sensor to measure the vibration is mounted on the springs. The signal from this sensor is fed back to the coil driver in such a manner that the oscillation of the system becomes self-exciting. A supplementary phase shift can be introduced into the feedback loop by means of a phase shifter which can be switched into and out of the circuit. The viscosity of the fluid in the gap between the housing and the rotor can be determined by comparing the difference in the oscillatory frequencies with the phase shifter switched in and out of the circuit to that obtained with calibration fluids of known viscosity. This viscometer has strong coupling effects in both the excitation system and in the mechanical resonator, so that an unknown and unpredictable damping is superimposed upon the damping caused by the fluid. Reliable measurements are therefore only possible when the apparatus is calibrated. Since the apparatus is meant for batch operation, it is primarily useful for laboratory measurements. A further viscometer with a phaseshifter in the feedback loop of a resonator has been described in "The Review of Scientific Instruments", Vol. 46, Nr. 11, Nov. 1975, p. 1560 ff. Here, the resonator is a vibrating string. This arrangement is primarily useful for laboratory measurements of fluids with known density in a relatively narrow range of viscosities.

SUMMARY OF THE INVENTION

An object of the present invention is to provide an improved viscometer.

A further object of the present invention is to provide a viscometer that can be used in production lines.

A still further object of the present invention is to provide a viscometer which does not require calibration with a reference fluid.

The viscometer of the present invention basically comprises a resonator vibrating parallel to its surface, a vibration exciter electrically connected to an oscillator, and a sensor for measuring the vibration of the resonator. The vibration exciter comprises a piezoelectric transducer rigidly attached to the resonator. The natural frequency of the transducer is substantially, i.e. by at least an order of magnitude, higher than the natural frequency of the resonator. Furthermore, the resonator is fastened at least on one of its ends to an inertial mass. That mass is connected by a spring to a housing element. The natural frequency of the resonator is substantially, i.e. by at least an order of magnitude, higher than the natural frequency defined by the inertial mass and the spring.

By this design cross coupling effects between the mechanical and electrical oscillations can be avoided. The inertial mass and the spring effectively isolate the resonator from external mechanical damping effects. Therefore, the viscosity of the fluid can be deduced directly from the result of the measurement. A reference fluid with known viscosity is not required. With the viscometer according to the present invention, a rapid and accurate measurement of the viscosity of a fluid in a wide range is achieved.

Further features and advantages of the present invention will become apparent from the following description of preferred embodiments of the invention which are described with reference to the accompanying drawings.

DESCRIPTION OF THE DRAWINGS

FIG. 1 is a longitudinal cutaway view of the probe.

FIG. 2 is a plan view of a transducer.

FIG. 3 is a polar diagram of the frequency response of the probe.

FIG. 4 is a schematic diagram of the circuit to which the probe is attached.

FIGS. 16–18 are forms of the resonator for special applications.

FIG. 19 is another form of resonator.

FIG. 20 is a further application.

FIG. 21 is a further variant of the torsional transducer.

FIG. 1 shows a measuring probe for the measurement of viscosity. It is composed of a resonator 2 which in turn consists of a circularly cylindrical tube 3 and a coaxial cylindrical rod 4. The upper end of tube 3 is fixed to the bottom of a massive housing 5 (by means of silver brazing, for example). The opposite lower end of the tube is attached by means of ring 6 to the lower end of rod 4 through a rigid and gas-tight seal, which seal may also be a silver-brazed joint. A coaxial piezoelectric sensor 7, as well as a coaxial piezoelectric exciter transducer 8 is cemented onto the end face of the upper end of the rod 4. Sensor 7 and exciter 8 are electrically insulated from one another and from rod 4 by means of insulating plates 9. The tube 3 is immersed in the fluid 10 to be measured, which is, for example a liquid.

FIG. 2 shows an end view of the exciter transducer 8. It consists of two piezoelectric ceramic plates 15 and 16 in the form of semicircular rings which are polarized oppositely to one another and parallel to the axis 11 of the probe 1. The surfaces of the disks 15 and 16 which face one another are provided with electrically conductive coatings 17 and 18 and are electrically connected to one another. Conductors 19 and 20 are connected to each of the coatings 17 and 18, respectively. If a voltage is applied across the conductors 19 and 20, the exciter becomes mechanically distorted in such a way that one face rotates through an angle with respect to the other about the axis 11 of the probe 1. A sinusoidal voltage applied to the conductors 19 and 20 forces the resonator to oscillate torsionally about its axis 11.

Figure 5:
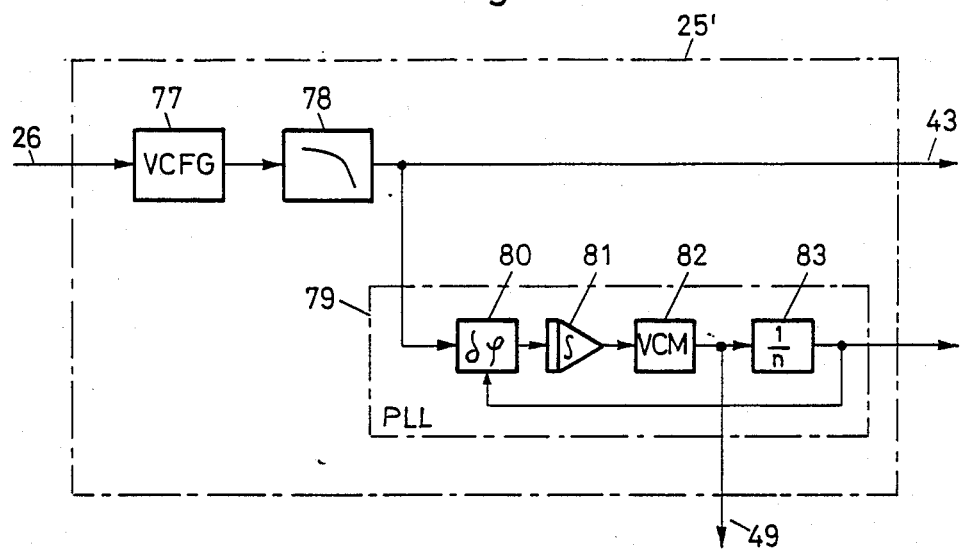
FIG. 5 is a variant of the circuitry shown in FIG. 4.

The sensor 7 is constructed in the same manner as exciter 8. In this case, shear stress on the half-rings produces a charge displacement which is impressed on the conductors 21 connected to the half-rings.

In FIG. 3, a polar diagram of the transfer function of the probe 1 is shown to clarify the basic principle of the damping measurement. On the abscissa R is plotted the real part, on the ordinate I the imaginary part of the transfer function, i.e. the ratio of the output angular displacement to the input torsional moment in the form $e^{i\omega t}$. With the oscillatory frequency f used as the parameter, the locus of the transfer function for small damping is approximated by a circle through the origin of the coordinate system with its midpoint on the ordinate axis I. The intersection $f_r$ of the locus of the transfer function with the ordinate axis defines the resonant frequency of the resonator 2, with a phase difference between the input and output oscillation of 90 degrees. The distance of the intersection point $f_r$ from the origin is dependent upon the damping of the resonator 2.

As shown in FIG. 4, the sinusoidal voltage applied to the conductors 19 and 20 of exciter 8 is produced by an oscillator 25. A control voltage at the input 26 of oscillator 25 controls its oscillatory frequency. One output of the oscillator 25 is connected to one of the inputs 27 of a phase sensitive detector (PSD) 28, whose other input, 29, is connected to the output of sensor 8 through an amplifier 30. The output voltage of the PSD 28 is proportional to the real part of the ratio of the output to the input of the resonator 2. The output voltage of the PSD 28 is integrated by means of integrator 31 and fed back to the control input 26 of oscillator 25. This integrating feedback forces the output voltage of the PSD 28 (and therefore the real part of the transfer function of the resonator 2) to zero, so that the vibrational frequency is stabilized exactly at the resonant frequency $f_r$.

If the signal from output 49 of oscillator 25 to input 27 of PSD 28 is phase-shifted through an angle $\partial\Phi$ by means of phase-shifter 35, this corresponds to a rotation of the coordinate system of the locus of the transfer function in FIG. 3 about the same angle $\partial\Phi$. In this case, assuming a resonant frequency $f_r$, the output of the PSD 28 is proportional to the projection of the point $f_r$ of the locus on the rotated abscissa. Because of the feedback, the output of PSD 28 will be integrated, and the frequency of the oscillator 25 proportionally shifted, until the output of the PSD 28, and therefore also the real part of the transfer function in the rotated coordinate system, returns to zero. The oscillator 25 now oscillates at the frequency $f_r - \partial f$.

The ratio of the frequency shift to the phase shift is, for small phase shifts, proportional to the damping of the resonator 2. When, therefore, the oscillatory frequency is measured for two discrete, predetermined values of the phase shift $\partial\Phi$ in the phase-shifter 35, (for example the values $\pm \partial\Phi$), the damping of the resonator can be immediately calculated from the difference of these two frequencies. When the resonator 2 is immersed in the fluid 10 to be measured, its damping is a continuous function of the viscosity of the fluid. The tube 3 of probe 1, which vibrates parallel to its surface, induces a co-oscillating boundary layer in the fluid, whose shear stress is proportional to the surface velocity of the tube 3 and therefore damps the resonator.

The oscillator 25 comprises a digital function generator and a digital to analog convertor 40 connected to said function generator's output. The values of a sinuoidal function with, for example, 256 values, are stored at sequential addresses of a read-only memory (ROM) 41. As the ROM 41 is sequentially addressed by the output of an 8-stage binary counter, a sinusoidal function appears at the inputs of the convertor 40 and is transformed by the convertor to an analog sinusoidal voltage output 43. The counter 42 is driven by a timing generator 44, which is realized as a voltage-controlled multivibrator, with a frequency which is 256 times as high as the desired output frequency. The input to the timing generator 44 is the control input 26 of the oscillator 25. The advantage of this described construction of oscillator 25 is that its sinusoidal output is derived directly from a square wave without the possibility of phase shifts arising, as would be the case when, for example, the sinusoid had to be derived from the square wave by means of filter circuits. In addition, a digital square wave signal is thereby provided which is exactly synchronous and in phase with the sinusoid. This makes it possible to construct phase-shifter 35 as a digital circuit.

In the present example of realization, the phase-shifter 35 also has an eight-stage binary counter 50 which counts the pulses of the timing generator 44 present on the second output 49 of the oscillator 25. The most significant binary stage of the counter 50 delivers a square wave which is exactly synchronous with the sinusoidal output of the oscillator 25. A phase shift can now be introduced by presetting the counter 50, at the start of each new counting cycle of counter 42 (i.e. when the output state of counter 42 becomes 00000000), to some initial value by means of preset circuit 51. If this initial value is given by n, and the sinusoidal oscillation consists of 256 intermediate values per period, then the phase shift is n×360°/256. In order to produce a phase shift symmetric with regard to the resonant frequency, the counting direction of the counter 50 is controlled by an independent square wave oscillator 52 which oscillates at a frequency $f_m$ which is much lower than the vibrational frequency $f_o$ the probe 1. When the output of the oscillator 52 is high, the counter 50 counts up. When the output of the oscillator 52 is low, the counter 50 counts down. One input of an exclusive OR gate 53 is connected to the output of counter 50; its other input is connected to the output of oscillator 52. Through this construction, the output of the phase shifter 35 is exactly synchronous with the output of oscillator 25 and shifted alternately positively and negatively by an exactly defined phase-angle. Depending on how the sensor 7 is constructed, i.e. according to whether it measures the angle, the angular velocity or the angular acceleration of the resonator, the preset circuit 51 can introduce an additional phase shift of 90° or 180°.

The phase-sensitive detector 28 comprises an inverting amplifier 58 and an electronic double-throw switch 59. The signal of the sensor 7 which is applied over amplifier 30 to the input 29 of the detector 28 is directly connected with one side, and connected over the inverter 58 to the other side of the switch 59. Said switch is actuated by means of the signal at input 27, i.e. the output of the phase shifter 35. If the digital input 27 of the detector 28 is shifted 90° with respect to the sinusoidal oscillation at input 29, then the average output voltage of the switch 59 is zero. Should however the phase-shift deviate from this value, the output voltage of switch 59 will be integrated by the integrator 31 and cause the timing generator to adjust the frequency in such a manner as to return the phase-shift to exactly 90 degrees.

For the evaluation of the measurement the impulses of the timing generator 44 are counted over equal time intervals at the two values of the phase shift. The difference of these two counts is proportional to the frequency difference $\partial f$ and therefore to the damping of the resonator 2. In order that the durations of the two counting periods be exactly equal, the oscillator 52 is driven by a stable frequency standard 63, e.g. a quartz oscillator. The frequency of this standard is divided down by counter 64. This output frequency of the counter 64 is again divided by two in a further counter stage 65. The output of counter stage 65 oscillates with the frequency $f_m$ and determines the counting direction of counter 50 as well as that of a further up-down counter 66 in the evaluation circuit 67. The output of an AND gate 68 is connected to the input of the counter 66, one input of said AND gate being connected to the output of counter 64 and the other input being connected to output 49 of timing generator 44. This construction causes the impulses of the timing generator 44 to be counted by counter 66 only during the second half of each half-period of the output of oscillator 52. This insures that there is sufficient time after the transition of the phase shift from one value to another for the system to adjust to its new frequency and amplitude. The counter 66 is reset to zero on each negative transition of the output of oscillator 52 after its contents have been transferred to output buffer 69. The value stored in buffer 69 can be displayed, for example, on a digital display 70. It is also possible to substitute a computer for the display 70, so that the measured viscosity can be determined directly from the contents of the buffer. In this computer can be stored, for instance, the characteristic curve of the probe 1 in the form of a polynomial approximation. The characteristic curve can be computed analytically by means of the Navier-Stokes equations.

FIG. 5 shows a variant with an oscillator 25' with analog circuitry. It comprises a voltage-controlled function generator 77 whose frequency depends on the voltage at input 26. The purity of the sinusoidal output of such commercially available function generators is generally insufficient for the present purpose and would tend to excite higher harmonics of the resonator 2, which harmonics would lead to measurement errors. For this reason the output of generator 77 is passed through a low-pass filter 78. Since filter 78 produces a frequency-dependent phase shift, the output 43 of the oscillator 25 is applied to the input of a phase-locked loop (PLL) 79 whose output is a square wave synchronous with and with zero phase shift with respect to said oscillator output 43. The PLL 79 comprises a phase-sensitive detector 80, an integrator 81, a voltage-controlled multivibrator 82 and a frequency divider 83. The flanks of its output serve to synchronize the phase-shifter 35 analogously to those of the counter 42 in FIG. 4. The output 49 of the multivibrator 82 is connected, analogously to the output 49 of multivibrator 44 in FIG. 4, to the counting input of phase-shifter 35 and the evaluation circuit 67. The output of the frequency divider 83 is synchronous with and has zero phase-shift with respect to the sine output 43.

Figure 6:
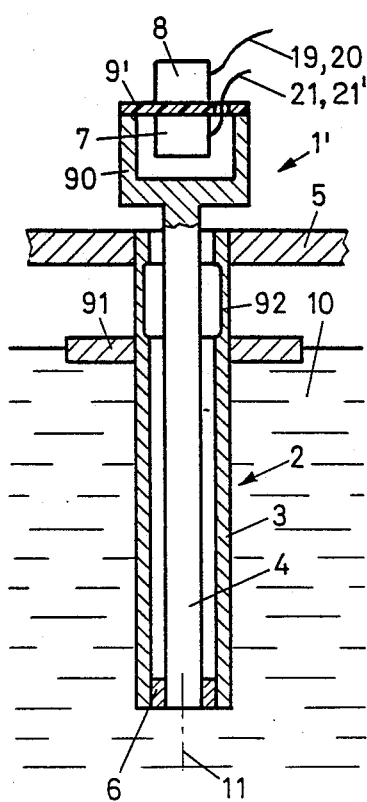
FIGS. 6–8 are longitudinal sections through three variants of the probe shown in FIG. 1.

FIG. 6 shows a variant of probe 1. This differs from the former for one in the arrangement of the exciter 8 and the sensor 7. To the face end of the bar 4 is attached a coaxial cup 90. The torsionally rigid insulating disk 9' is cemented to the rim of the face end of the cup 90 and the exciter 8 and the sensor 7 are cemented to the two sides of disk 9', respectively. While in the embodiment in FIG. 4 the sensor measures, besides the angular acceleration of the bar the moment transmitted to the bar 4 by the exciter 8, the sensor 7 in the embodiment in FIG. 6 is essentially a pure angular acceleration sensor. It has the advantage that the sensor 7 responds only to motion of the cup 90 as transmitted by the torsionally rigid insulating disk 9' and is unaffected by the motion of the exciter 8, except insofar as this motion is effective in causing torsional oscillations of the rod 4. The sensor 7 is thereby effectively isolated from direct transmission of motion from exciter 8, which otherwise would result in phase errors in the signal delivered by sensor 7. This has the beneficial effect that for frequencies far from the resonance frequency of resonator 1 the output of sensor 7 is zero.

In addition, a rotationally symmetric inertial mass 91 is affixed to the tube 3 of probe 1 in the neighborhood of the housing-bottom 5. The tube 3 has a region 92 with reduced torsional rigidity between the inertial mass 91 and the housing-bottom 5. This construction is especially expedient when very low values of the viscosity of fluid 10 are to be measured, because at low values of damping of the resonator 2 the vibrations transferred to the housing and subjected there to unpredictable damping tend to disturb the measurement. The inertial mass 91 vibrationally isolates the resonator 2 from the housing-bottom.

Figure 7:
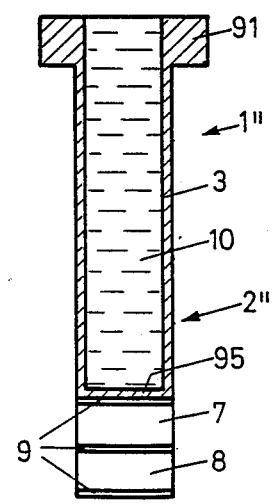
Figure 8:
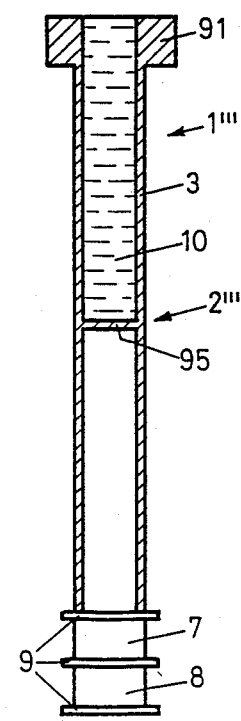

In the variant represented in FIG. 7, the resonator 2 of the probe 1 consists simply of the tube 3 which is closed at its lower end by a disk-shaped bottom 95. Insulating disks 9, the sensor 7 and the exciter 8 are cemented to the lower side of this bottom 95. An inertial mass 91 is again affixed to the tube 3. This is joined with the housing, for example in the manner shown in FIG. 6. The fluid to be measured is here introduced into the interior of the tube 3. The probe 1'' is therefore especially suited to cases where only small amounts of fluid are available. The probe 1''' shown in FIG. 8 corresponds to that shown in FIG. 7, except that the bottom-disk 95 has been positioned at a vibrational node of resonator 2'''.

Figure 9:
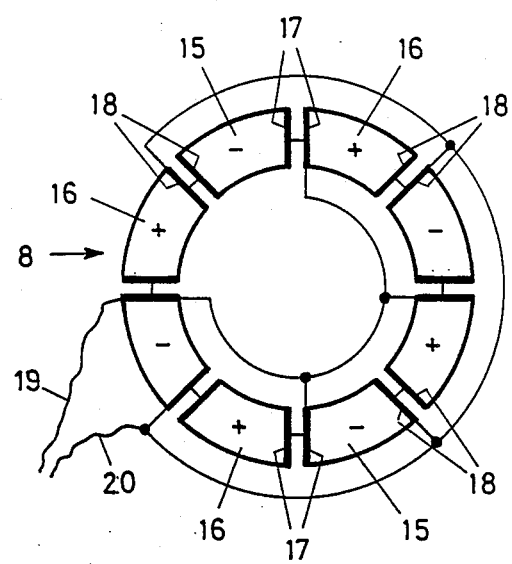
FIGS. 9–11 are three further variant forms of vibrational exciter transducers.

FIG. 9 shows a further embodiment of transducer 8. The exciter is built up from eight circular ring segments 15 and 16 arranged in a ring with alternating opposite polarizations and electrically connected with one another. Used as a vibrational exciter, this embodiment produces a greater vibrational amplitude for the same input voltage compared with the embodiment shown in FIG. 2. It also shows a greater sensitivity when used as sensor 7. In the embodiment in FIG. 9, it is, however, also possible to use, for example, two oppositely situated segments 15 or 16 as a sensor, and the remaining six segments as a vibrational exciter.

Figure 10:
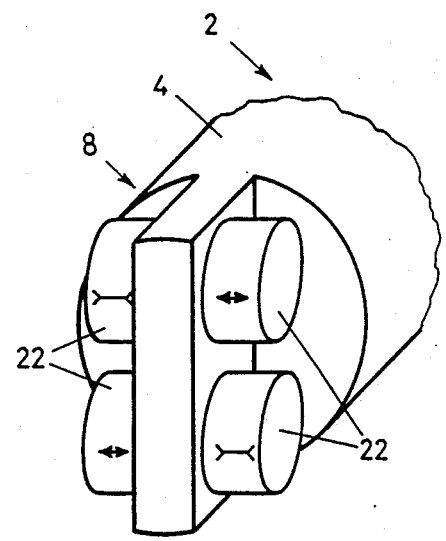

In the embodiment in FIG. 10, four piezo-electric ceramic thickness transducers are arranged on the face-end of the bar 4 of the resonator 2. Two each of the diametrically opposed transducers 22 are excited in phase, while the remaining two transducers are excited in counterphase. Here, too, the sensor 7 (not shown) can be constructed analogously to the exciter 8. It is also possible, however, to use two of the diametrically opposed thickness transducers 22 as sensors.

Figure 11:
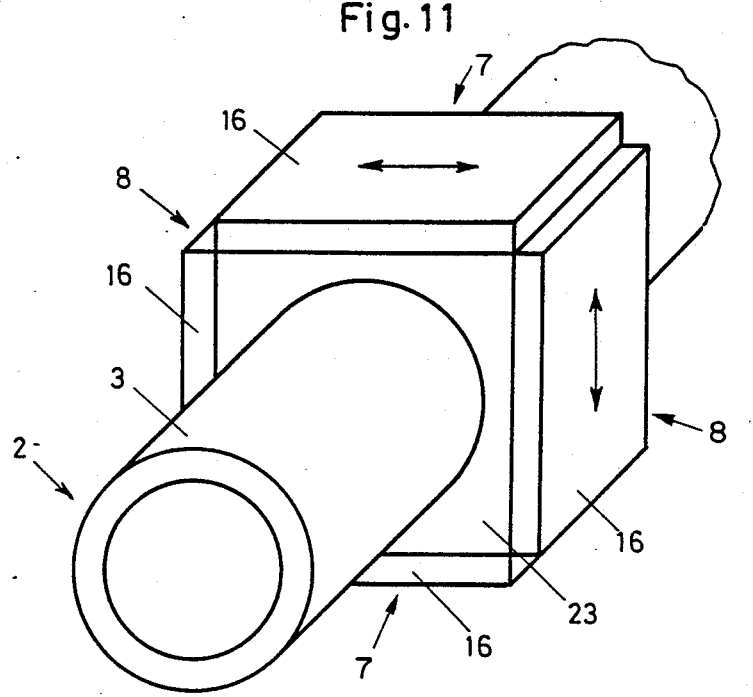

The embodiment in FIG. 11 corresponds essentially to that in FIG. 9, except that here the piezoelectric shear-plates 16 are attached to the side faces of a regular polygonal prism 23 attached coaxially to the tube 3 of resonator 2.

Figure 12:
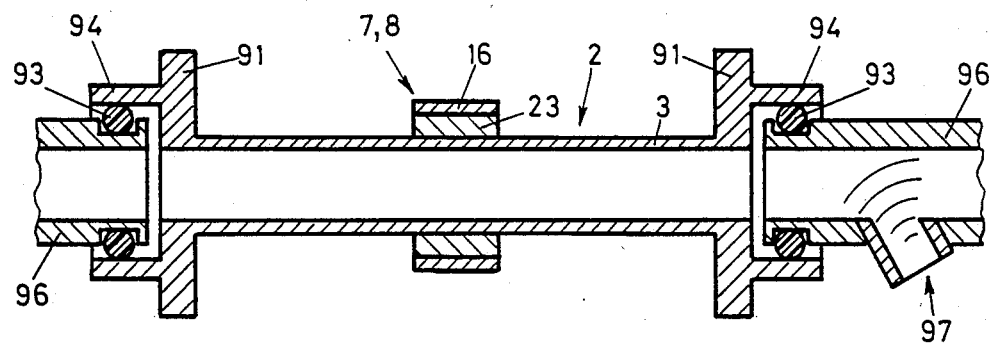
FIG. 12 is another form of probe.

The embodiment of transducer 8 in FIG. 11 is especially expedient in the embodiment of resonator 2 according to FIG. 12. Here, the resonator comprises simply the tube 3 which is fastened at each end into an inertial mass 91. From each inertial mass 91 and coaxial with same protrudes, on the side away from tube 3, a tube-shaped projection 94. This is elastically supported on an elastomeric O-ring 93. The O-ring 93 is seated in a circumferential groove of a connecting tube 96. In the example shown the prism 23 of the transducer 8 is attached at the middle of the tube 3. When the tube is excited at its torsional resonant frequency, nodes form at the two inertial masses and an amplitude maximum occurs at the middle of the tube. Vibrational isolation from the environment is provided by the torsionally compliant O-rings 93 in combination with the inertial masses 91. It is advantageous that the natural frequency of the resonator 2 be several orders of magnitude higher than the natural frequency defined by the spring constant of the O-rings 93 and the inertial masses 91. Through this construction the resonator can be effectively isolated from the damping influences of the connecting tubes 96.

The embodiment according to FIG. 12 makes possible the measurement of the viscosity of a fluid flowing through the tube 3, e.g. a flowing liquid. An ultrasound sensor 97 is represented schematically built into the right connecting tube 96, with which sensor the velocity profile of the fluid over the cross section of the tube 3 may be determined for the purpose of determining the dependence of the viscosity upon the shear gradient. Instead of being disposed at half the length of the tube 3 the exciter transducer 8 can be placed one-quarter of the tube length from one of the inertial masses 91. It is thereby possible to excite the second harmonic of the fundamental natural frequency of tube 3. In this case, exciter 8 and sensor 7 can be spatially separated from one another and fastened at the two vibrational antinodes, respectively. It is also possible in the embodiment in FIG. 12 to employ a longitudinal vibration in the direction of the axis of tube 3 instead of a torsional vibration of tube 3. For this purpose it would be possible, for example, to turn the piezoelectric plates 16 of the embodiment according to FIG. 11 through 90 degrees about an axis perpendicular to the plane of each piezoelectric plate 16 and passing through its geometric center such that the direction of polarization of the piezoelectric plates 16 is parallel to the longitudinal axis of the tube 3.

Figure 13:
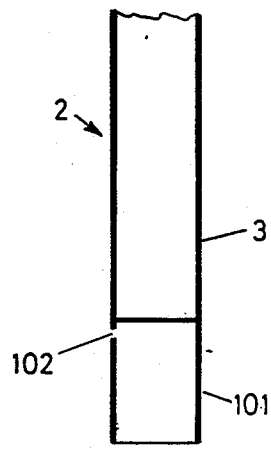
FIGS. 13–15 are probes showing means of varying the effective surface area of the resonator.
Figure 14:
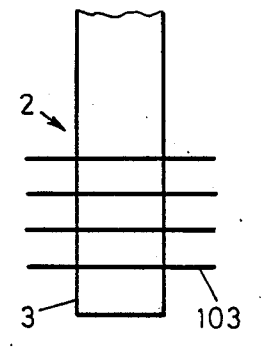

In FIGS. 13 and 14, two possibilities are represented for enlarging the surface area of the resonator 2 which is wet by the fluid to be measured. This is especially advantageous for measurements of fluids with very small viscosities. In the embodiment in FIG. 13 the tube 3 has a tubular extension 101. An opening 102 allows trapped air to escape from this extension when the resonator 2 is submerged into a liquid. In the variant in FIG. 14, circular annular lamina 103 are fastened to the tube 3 of the resonator 2.

Figure 15:
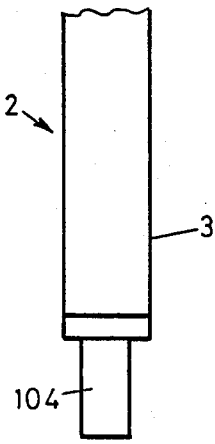

In the embodiment in FIG. 15, a cylindrical extension 104 is detachably fastened to the lower end of the tube 3 of the resonator by means e.g. of a screw thread or a fast-acting adhesive. The extension 104 is meant as a disposable tip. This embodiment is suited, for example, for measuring the viscosity of a synthetic resin during the hardening process.

In the embodiment in FIG. 16 the fluid to be measured is filled into a cylindrical vessel 107. The vessel 107 is coaxial to the tube 3 of the resonator 2. It is seated on a coaxial shaft 108 which is driven either with an adjustable angular velocity or an adjustable torque. This embodiment is thereby suited for determining the viscosity of thixotropic substances.

The embodiment in FIG. 18 is built analogously to that in FIG. 6, except that the tube 3 has at its lower end a solid cylindrical coaxial extension 109. This embodiment is advantageous mainly for measurements in high-viscosity ranges. The neck 92 is again constructed so as to be very torsionally compliant, so that the natural frequency determined by the elastic constant of said neck and the moment of inertia of the inertial mass 91 lies at least one order of magnitude lower than the natural frequency of resonator 2. When this neck 92 is constructed of metal, damping alloys, e.g. ferromagnetic iron-chromium-aluminum alloys, are especially suited to the purpose.

In FIG. 17 an embodiment is shown for measurement of the viscosity of small samples of liquids. The resonator 2 has been inverted and has its free end uppermost. A flange 111 with a planar end face 112 is attached to the upper end of tube 3. A disk 113 is attached to a shaft 115 coaxially to said shaft and to flange 111. The face surface 114 of disk 113 facing the face surface 112 of flange 111 is slightly conical. There is a minute gap between the tip of this cone and the face surface 112. A drop of test fluid introduced between the surfaces 112 and 114 centers itself by capillary action. The embodiment in FIG. 17 is especially suited to measurement of higher viscosities. When the shaft 115 is turned, the dependence of viscosity on shear velocity may again be investigated.

In the embodiment in FIG. 19, the resonator is constructed as a circular flat metallic membrane 119. The membrane 119 is clamped between two rings 118. The test liquid 120 may, for example, be simply applied to the membrane 119 as a thin film. A ring-shaped coating 121 of liqid-repellent material, e.g. silicone rubber, may be applied to the membrane in order to center the liquid 120. A cup-shaped carrier 122 is fastened to the underside of the membrane 119. This carrier carries, analogously to the insulating disk in FIG. 6, the exciter 8 and the sensor 7. The transducer 8 induces a torsional vibration in the membrane 119 and comprises, for example, plates 15 and 16 corresponding to the embodiment of FIG. 2 or FIG. 9. In addition a thickness-mode transducer 123 can be fastened centrally to the carrier 122 to excite vibrations of the membrane perpendicular to its surface. The vibrations can be measured by another sensor 124. These vibrations directed perpendicular to the surface of the membrane 119 enable the additional measurement of the density of the test fluid 120.

In the embodiment in FIG. 20, two resonators 2 are fastened coaxially and in diametrical opposition to the lower, free end of a tubular shaft 129. The vibrational exciters 8 of these resonators 2 may be excited with 180 degrees phase shift with respect to one another. The two resonators 2 therefore constitute a torsional tuning fork. When the shaft 129 is turned the two resonators 2 function as an agitator. The viscosity of thixotropic material, e.g. unset concrete, can thereby also be investigated.

FIG. 21 shows a further embodiment of transducer 8. It differs from the transducer 8 in FIG. 2 in that the piezoelectric disk segments 15' and 16' are only quarter-circle segments mounted on the periphery of bar 4, and radially polarized. Here the polarization directions 132 and 133 alternate, and are therefore directed alternately inward and outward on successively following segments 15' and 16'.

The process described is generally suited for the measurement of the damping of a resonator. Under the term "fluid" fall gases, Newtonian and non-Newtonian liquids as well as viscoelastic substances. Further phase sensitive detectors comprise e.g. an analog multiplier or an exclusive-OR gate, in which case the analog signal of the sensor 7 is applied over an amplifier and a limiter to one input of the gate. The book "Theorie und Anwendung des Phase Locked Loop" by Roland Best, AT-Verlag, Aarau Switzerland 1981 describes various circuits which may be used for the phase locked loop 79 as well as for the phase sensitive detector 28.

What is claimed is:

1. A viscometer comprising, a resonator having a contact surface in contact with a fluid the viscosity of which is to be measured, the resonator vibrating parallel to its contact surface over the entire area of the contact surface, a vibration exciter electrically connected to an oscillator, and a sensor for measuring the vibration of the resonator, said vibration exciter comprising a piezoelectric annular shear transducer comprising a plurality of individual segments rigidly attached to said resonator, the natural frequency of said transducer being substantially higher than the natural frequency of said resonator.

2. A viscometer according to claim 1 wherein said resonator is fastened at least on one of its ends to an inertial mass which is connected by an element of reduced rigidity to a housing, and wherein the natural frequency of said resonator is substantially higher than the natural frequency defined by the inertial mass and the spring rate of said element.

3. A viscometer according to claim 1, wherein said sensor is a piezoelectric segmented inertial annular shear transducer.

4. A viscometer according to claim 1, wherein said resonator comprises a rotationally symmetric torsional vibrator vibrating about an axis of said resonator.

5. A viscometer according to claim 1, wherein said resonator is a flat, circular membrane.

6. A viscometer according to claim 4, further comprising a second, identical resonator with a second, identical transducer and a second, identical sensor, the first and second resonator being axially aligned and forming, together, a torsional tuning fork that is rotatable about an axis crossing the axis of the resonators.

7. A viscometer comprising, a resonator having a contact surface in contact with a fluid the viscosity of which is to be measured, the resonator vibrating parallel to its contact surface over the entire area of the contact surface, a vibration exciter electrically connected to an oscillator, and a sensor for measuring the vibration of the resonator, said vibration exciter comprising a piezoelectric annular shear transducer comprising a plurality of individual segments rigidly attached to said resonator, the natural frequency of said transducer being substantially higher than the natural frequency of said resonator, including a feedback circuit for stabilizing the vibration frequency of the resonator, comprising said oscillator, the frequency of which is controllable by an input signal on its input and the output of which is connected to the vibration exciter and, via a phase shifter that shifts the phase of its input oscillation by one of two selectably switchable values, with a phase-sensitive detector whose second input is connected to said sensor, and whose output is fed back over an integrator to the control input of said oscillator, and wherein the viscometer contains an evaluating circuit which determines the difference of the vibration frequency of the resonator at the two values of the phase shift.

8. A viscometer comprising, a resonator having a contact surface in contact with a fluid the viscosity of which is to be measured, the resonator vibrating parallel to its contact surface over the entire area of the contact surface, a vibration exciter electrically connected to an oscillator, and a sensor for measuring the vibration of the resonator, said vibration exciter comprising piezoelectric annular shear transducer comprising a plurality of individual segments rigidly attached to said resonator, the natural frequency of said transducer being substantially higher than the natural frequency of said resonator, wherein said resonator comprises protrusions to enlarge its surface.

9. A viscometer comprising, a resonator having a contact surface in contact with a fluid the viscosity of which is to be measured, the resonator vibrating parallel to its contact surface over the entire area of the contact surface, a vibration exciter electrically connected to an oscillator, and a sensor for measuring the vibration of the resonator, said vibration exciter comprising a piezoelectric annular shear transducer comprising a plurality of individual segments rigidly attached to said resonator, the natural frequency of said transducer being substantially higher than the natural frequency of said resonator, wherein said resonator comprises a pipe open on both ends for the flow of fluid there through, wherein said vibration exciter is fastened to the outer surface of said pipe between its two ends.

10. A viscometer comprising, a resonator having a contact surface in contact with a fluid the viscosity of which is to be measured, the resonator vibrating parallel to its contact surface over the entire area of the contact surface, a vibration exciter electrically connected to an oscillator, and a sensor for measuring the vibration of the resonator, said vibration exciter comprising a piezoelectric annular shear transducer comprising a plurality of individual segments rigidly attached to said resonator, the natural frequency of said transducer being substantially higher than the natural frequency of said resonator, further compromising a rotationally symmetric containment coxially arranged to the resonator axis, the fluid to be measured being located between said containment and said resonator, said containment being rotatable about said axis relative to said resonator.

* * * * *